United States Patent
Hubbell

[11] Patent Number: 6,074,367
[45] Date of Patent: Jun. 13, 2000

[54] PREINSERTION MEASUREMENT OF CATHETERS

[75] Inventor: Randolph W. Hubbell, Northborough, Mass.

[73] Assignee: Scimed Life Systems, Inc., Maple Grove, Minn.

[21] Appl. No.: 09/163,152

[22] Filed: Sep. 29, 1998

Related U.S. Application Data

[60] Provisional application No. 60/060,625, Oct. 1, 1997.

[51] Int. Cl.$^7$ .................................................. A61M 5/178
[52] U.S. Cl. ........................ 604/164; 604/117; 600/585; 206/364
[58] Field of Search .................................... 604/164, 161, 604/117, 116; 600/585, 434; 33/755, 756; 206/570, 571, 364

[56] References Cited

U.S. PATENT DOCUMENTS

| | | | |
|---|---|---|---|
| 4,653,194 | 3/1987 | Kim | 33/429 |
| 4,660,560 | 4/1987 | Klein . | |
| 5,007,898 | 4/1991 | Rosenbluth et al. . | |
| 5,030,227 | 7/1991 | Rosenbluth et al. . | |
| 5,050,430 | 9/1991 | Begin et al. | 73/292 |
| 5,107,869 | 4/1992 | Henry | 132/213.1 |
| 5,158,084 | 10/1992 | Ghiatas | 604/164 |
| 5,239,982 | 8/1993 | Trauthen | 128/4 |
| 5,257,972 | 11/1993 | Gurmarnik | 604/51 |
| 5,297,546 | 3/1994 | Spofford et al. | 604/51 |
| 5,312,430 | 5/1994 | Rosenbluth et al. . | |
| 5,353,808 | 10/1994 | Viera | 604/164 |
| 5,479,938 | 1/1996 | Weier | 128/657 |
| 5,527,336 | 6/1996 | Rosenbluth et al. . | |
| 5,752,971 | 5/1998 | Rosenbluth et al. . | |
| 5,836,951 | 11/1998 | Rosenbluth et al. . | |

FOREIGN PATENT DOCUMENTS

| | | |
|---|---|---|
| 1330187 | 6/1994 | Canada . |
| 0723786A1 | 7/1996 | European Pat. Off. . |
| 0417189B1 | 10/1997 | European Pat. Off. . |
| 95/12427 | 5/1995 | WIPO . |

*Primary Examiner*—Corrine McDermott
*Attorney, Agent, or Firm*—Testa, Hurwitz & Thibeault, LLP

[57] ABSTRACT

Kits and methods of the invention provide for preinsertion measurement of a catheter and tunnel lengths required to position the tip of a catheter, such as a dialysis catheter, at a desired location within a body vessel or lumen, such as a vein. Kits of the invention include a wire of predetermined length which has a tip, a proximal end, and a plurality of markings at predefined intervals. The wire is inserted into a body vessel so that the tip of the wire is positioned at the desired catheter tip location. The number of markings on the portion of the wire remaining outside the body are then counted and used to calculate the length of wire either outside or inside the body. This length of wire may be found in a conversion chart, which is also included in the kit, and matched to a corresponding catheter and tunnel lengths or catheter code. Methods of the invention include inserting the wire having predetermined length, tip, proximal end and markings at predefined intervals in a vessel, positioning the wire at the desired catheter tip location using an imaging method, such as fluoroscopy, counting the number of markings remaining outside the body, and determining the catheter and tunnel lengths required based on the number of markings. The determination of the catheter and tunnel lengths required may also be performed using a conversion chart.

22 Claims, 3 Drawing Sheets

PREINSERTION MEASUREMENT OF CATHETERS

CROSS-REFERENCE TO RELATED APPLICATION

This incorporates by reference and claims priority to and the benefit of U.S. provisional patent application Ser. No. 60/060,625, which was filed on Oct. 1, 1997.

TECHNICAL FIELD

The invention relates generally to inserting a tunneled device into a body. More particularly, the invention relates to kits and methods for performing preinsertion measurements to determine a proper length chronic dialysis catheter for insertion into a body.

BACKGROUND INFORMATION

In general, chronic dialysis catheters are fixed-length, dual-lumen catheters that cannot be trimmed or adjusted at either the distal or proximal ends. These types of catheters are tunneled under the skin to a venotomy site and placed in a large central vein (e.g., the jugular vein).

The process of determining the proper length for the tunnel (i.e., length from outside the body to the venotomy site) and the proper length catheter for placement in the vein to ensure that the tip is at the desired location (e.g., the right atrium or the superior vena cava and right atrial, or SVC/RA, junction) is quite crude and imprecise. Typically, a physician places the catheter on the exterior of the patient's body and estimates the location of the heart. The catheter is then stretched out to emulate the tunnel. This crude process is used by the physician to obtain the "proper" length for the catheter.

A problem with this approach, however, is that it does not always provide the physician with the exact catheter tip placement that he/she desires. In addition, chronic dialysis catheters come in various lengths to suit different anatomical needs, and the sterile catheter kit that has been opened sometimes contains a catheter that is too short or too long. Further, sterile catheter kits must then be opened until the proper length catheter is found, thereby wasting catheters and increasing costs. Another problem with this approach is that the physician may create a tunnel of incorrect length and then need to create a new tunnel suitable for the catheter length selected. Creating a new tunnel increases the risk of infection and hematoma and increases the procedure time.

SUMMARY OF THE INVENTION

The invention relates generally to kits and methods for preinsertion measurement of the length of a tunneled catheter (e.g., chronic dialysis catheter, central port with a preattached catheter, or tunneled central catheter with a sterilized tip, such as a valve) needed for placement in a vessel or lumen of a body. The invention can also provide for preinsertion measurement of the length of any other device that must be tunneled and that must be trimmed to a length optimal for the patient's physique. Kits and methods of the invention also relate to preinsertion measurement of the length of the tunnel from the entry site to the vessel as required. With kits and methods according to the invention, the sterile kit in which the catheter is stored need not be opened until after the proper catheter and tunnel lengths are determined, thereby reducing waste and costs.

The kits and methods of the present invention provide for preinsertion measurements to determine proper catheter and tunnel lengths for insertion of a catheter into a vessel of a body. A proper catheter length is the length of catheter required to ensure that the tip of the catheter is at the desired location following insertion of the catheter in the vessel. A proper tunnel length is the length of the tunnel (i.e., distance that the catheter must be tunneled under the skin from the entry site to the vessel) required to ensure that the tip of the selected catheter will be positioned at the desired location following insertion of the catheter in a body. The desired catheter tip location may be, for example, the right atrium or the SVC/RA junction. The catheters may include, but are not limited to, chronic dialysis catheters, central ports, and tunneled central catheters. Furthermore, the catheters may be designed to be attached to a subcutaneously implanted port.

Kits according to the invention can include a wire of predetermined length and having a tip, a proximal end, and a plurality of markings along its length. The markings are spaced at predefined intervals along the length of the wire. In one embodiment, the tip of the catheter is radio-opaque. The wire is inserted into a vessel of a body so that the tip of the wire is positioned at a desired catheter tip location.

Kits of the invention also can include a conversion chart. Once the wire is inserted into the vessel, the number of markings on the portion of the wire remaining outside of the body is counted. This number of markings is then used to determine the length of wire outside the body, which is then converted to proper catheter and tunnel lengths by matching the length of wire outside the body with catheter and tunnel lengths on the conversion chart. Alternatively, the number of markings is used to determine the length of wire inside the body, which is also converted to proper catheter and tunnel lengths by matching the length of wire inside the body with catheter and tunnel lengths on the conversion chart.

In one embodiment, the conversion chart includes a plurality of codes, and each of the codes corresponds to a catheter having a particular length. In this embodiment, the length of wire, either inside or outside the body, is matched to a code for a catheter having the proper catheter length. The proper tunnel length for the selected code may then be identified by reference to the chart. In other embodiments of the invention, the kits include any one, more than one, or all of the following items: an entry needle; a coaxial dilator assembly or peelable sheath/dilator assembly; and a sterile ruler.

Methods according to the invention include inserting a wire of predetermined length into a vessel of a body. The wire has a tip that preferably is radio-opaque, a proximal end, and a plurality of markings. Each of the markings are at a predefined interval along the length of the wire. Using an imaging technique, such as, for example, fluoroscopy or ultrasound, the tip of the wire is positioned at a desired catheter tip location. The number of markings along the wire that remain outside the body are then counted to determine the length of wire outside of the body. In an alternative embodiment, this number of markings is used to determine the length of wire in the vessel of the body, which thereby provides the distance from the desired catheter tip location to the entry site. Based on the number of markings, a proper catheter length is thus determined.

In one embodiment of a method of the invention, a conversion chart is used to match the length of wire outside the body (or, alternatively, inside the body) to proper catheter and tunnel lengths. The conversion chart can provide catheter codes that correspond to catheters of various lengths. The codes indicate the catheter to use (i.e., the codes vary based on the length of the catheter) and the distance from the tunnel entry site to the venotomy. The length of wire outside the body (or, alternatively, inside the body), which is based on the number of markings, can then be matched to a code which corresponds to a catheter having the proper catheter length. Thus, the physician, operator, or assistant can easily locate the code on the chart and select a catheter having the proper catheter length. The chart also provides the proper tunnel length required for the selected catheter.

The invention thus provides for preinsertion measurements to determine proper catheter and tunnel lengths. The proper catheter length can be determined before having to open sterile catheter kits, thereby reducing costs and waste. Furthermore, the proper tunnel length can be determined before creating the tunnel, thereby reducing the likelihood of having to create a second tunnel, which, in turn, reduces the risk of infection and hematoma.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Kits and methods are provided for performing preinsertion measurements of proper catheter and tunnel lengths. In some embodiments of the invention, the catheters are chronic dialysis catheters, but they may also be central ports or tunneled central catheters. Furthermore, the catheters may be preattached to a subcutaneously implanted port. A proper catheter length is the length of catheter required to ensure that the tip of the catheter is at the desired location following insertion of the catheter in a vessel or lumen of a body. The vessel or lumen can be any body lumen such as, for example, a blood vessel, a vein, or some other part of the vasculature, but it typically will be a vein. A proper tunnel length is the length of the tunnel (i.e., distance that the catheter must be tunneled under the skin from the entry site to the vessel) required to ensure that the tip of the selected catheter will be positioned at the desired location following insertion of the catheter in a body. The desired catheter tip location can be, for example, the right atrium or the SVC/RA junction.

Figure 1:
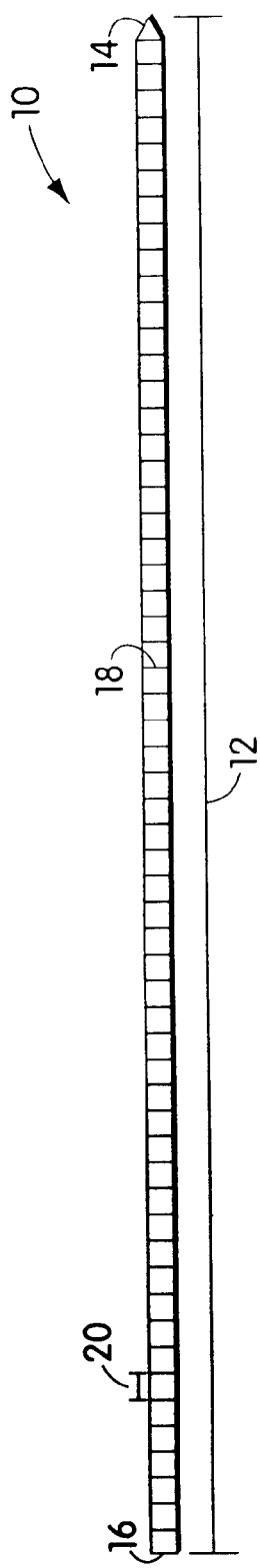
FIG. 1 is an illustration of a wire for use in kits and methods of the invention.

A kit of the invention includes a wire and a conversion chart. A wire for use in a kit of the invention is shown in FIG. 1. The wire 10 has a predetermined length 12. The predetermined length 12 of the wire 10 is based on practical considerations, such as anatomical dimensions and the procedure being performed. For example, a kit for use in performing a preinsertion measurement for insertion of a catheter in an internal jugular vein would have a wire with a predetermined length of about 60 cm. Wires of other predetermined lengths can, however, be used.

A wire 10 in a kit of the invention also has a tip 14, a proximal end 16, and a plurality of markings 18. The tip of the wire preferably is radio-opaque, but may be modified in any manner suitable to allow imaging of the tip of the wire after its insertion into a vessel of a body.

The markings 18 on the wire 10 are each at a predefined interval 20 along the wire. The markings 18 are each spaced the same distance apart on the wire 10. The predefined interval 20 can be of any distance. The markings 18 on the wire 10 allow for the determination of proper catheter and tunnel lengths when used in conjunction with a conversion chart. The wire 10 of the kit is inserted in a vessel of a body so that the tip 14 of the wire 10 is positioned at a desired catheter tip location. The wire tip 14 may be positioned by the use of an imaging technique, such as fluoroscopy or ultrasound, for example. Other imaging techniques may also be used to position the wire tip 14.

After insertion of the wire 10, the number of markings 18 on the wire 10 remaining outside the body are counted. Since the markings 18 are spaced at predefined intervals 20 on the wire 10, counting the number of markings 18 allows a user to determine the length of wire outside the body. For example, the number of markings 18 may be multiplied by the distance between intervals to determine the length of wire remaining outside the body after insertion. Alternatively, the length of wire inside the body may be calculated by subtracting the length of wire outside the body from the overall predetermined length of the wire. The length of wire remaining outside the body (or, alternatively, inside the body) is then located on a conversion chart. In one embodiment, a proper catheter length and associated proper tunnel length is then determined by matching the length of wire to the numbers given on the chart. Alternatively, the proper catheter length may be selected from the chart if the tunnel length is in some way fixed.

In one embodiment, the conversion chart contains a plurality of codes, which each correspond to a catheter having a particular length. In this embodiment, the length of wire (either inside or outside the body) is matched to a corresponding code to determine which catheter, and, hence, which catheter length, to use.

Table 1 shows a conversion chart of the invention. The left-hand side of the chart includes lengths of wire remaining outside the body. Following a line from the length of wire outside the body across the chart provides corresponding catheter codes and tunnel lengths. A conversion chart, such as the one shown as Table 1, allows a physician to select a catheter length and corresponding tunnel length based on the amount of wire outside of the body. The code indicates the catheter to use (i.e., the codes for the catheters vary based on length). The distance of the tunnel entry site from the venotomy is tabulated for each catheter code based on the amount of wire outside the vein. A tunnel length is typically between about 4 cm and about 8 cm. For example, if after positioning the wire tip at the desired catheter tip location, 44 cm of wire is found to be remaining outside the body, Product Code A is selected for the catheter and a 4 cm tunnel is required to appropriately position the catheter tip.

TABLE 1

| Wire Length Outside Body | Product Code A (19 cm tip to cuff) | Product Code B (24 cm tip to cuff) | Product Code C (28 cm tip to cuff) |
|---|---|---|---|
| 32 cm | | | |
| 33 cm | | | 2 cm |
| 34 cm | | | 3 cm |
| 35 cm | | | 4 cm |
| 36 cm | | | 5 cm |
| 37 cm | | 2 cm | 6 cm |
| 38 cm | | 3 cm | 7 cm |
| 39 cm | | 4 cm | 8 cm |
| 40 cm | | 5 cm | 9 cm |
| 41 cm | | 6 cm | 10 cm |
| 42 cm | 2 cm | 7 cm | |
| 43 cm | 3 cm | 8 cm | |
| 44 cm | 4 cm | 9 cm | |
| 45 cm | 5 cm | 10 cm | |
| 46 cm | 6 cm | | |
| 47 cm | 7 cm | | |
| 48 cm | 8 cm | | |
| 49 cm | 9 cm | | |
| 50 cm | 10 cm | | |

(Right margin label: TUNNEL LENGTH)

Figure 2:
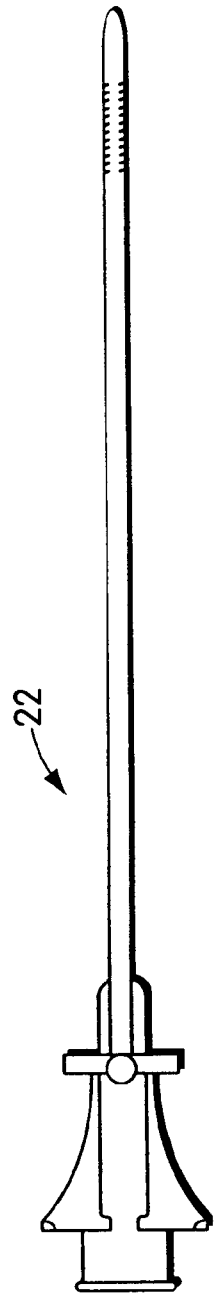
FIG. 2 is an illustration of an entry needle for use in kits and methods of the invention.
Figure 3A:
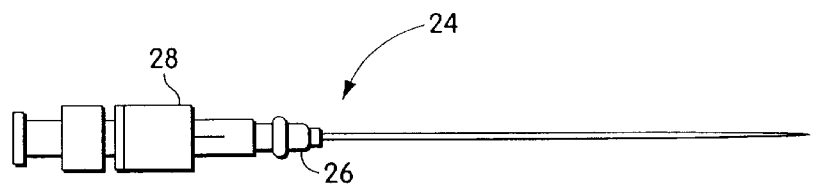
FIG. 3A is an illustration of a coaxial dilator assembly for use in kits and methods of the invention.
Figure 3B:
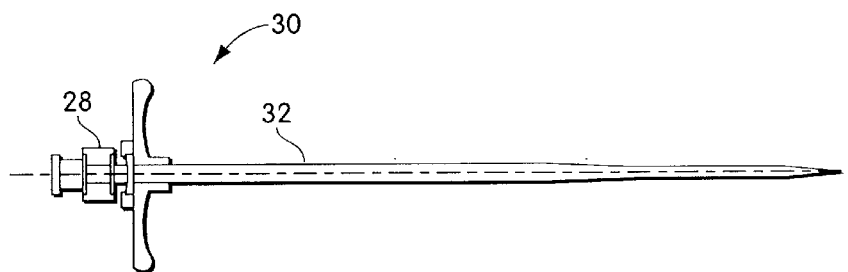
FIG. 3B is an illustration of a peelable sheath/dilator assembly for use in kits and methods of the invention.
Figure 4:
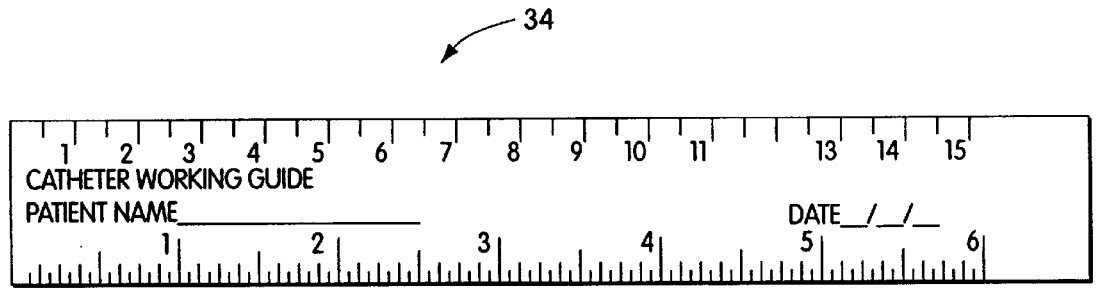
FIG. 4 is an illustration of a sterile ruler for use in kits and methods of the invention.

In other embodiments, kits of the invention include any one, more than one, or all of the following: an entry needle; a coaxial dilator or peelable sheath; and a sterile ruler. An entry needle for use in a kit or method of the invention is shown at FIG. 2. The entry needle 22 may be used to puncture the skin of the patient and thereby create the entry site for the catheter. A coaxial dilator assembly for use in a kit or method of the invention is shown at FIG. 3A. The coaxial dilator assembly 24 includes an outer dilator 26, which fits over an inner dilator 28. The coaxial dilator assembly may be used to predilate the venotomy and exchange the insertion wire for a second, larger wire, if needed. A peelable sheath/dilator assembly for use in a kit or method of the invention is shown in FIG. 3B. The peelable sheath/dilator assembly 30 includes peelable sheath 32, which fits over dilator 28. The peelable sheath/dilator assembly may be used to dilate the venotomy and introduce the catheter. A sterile ruler for use in a kit or method of the invention is shown at FIG. 4. The sterile ruler 34 may be used to determine the location on the body to create the entry site for the catheter by measuring the length of the tunnel from the venotomy site.

Figure 5:
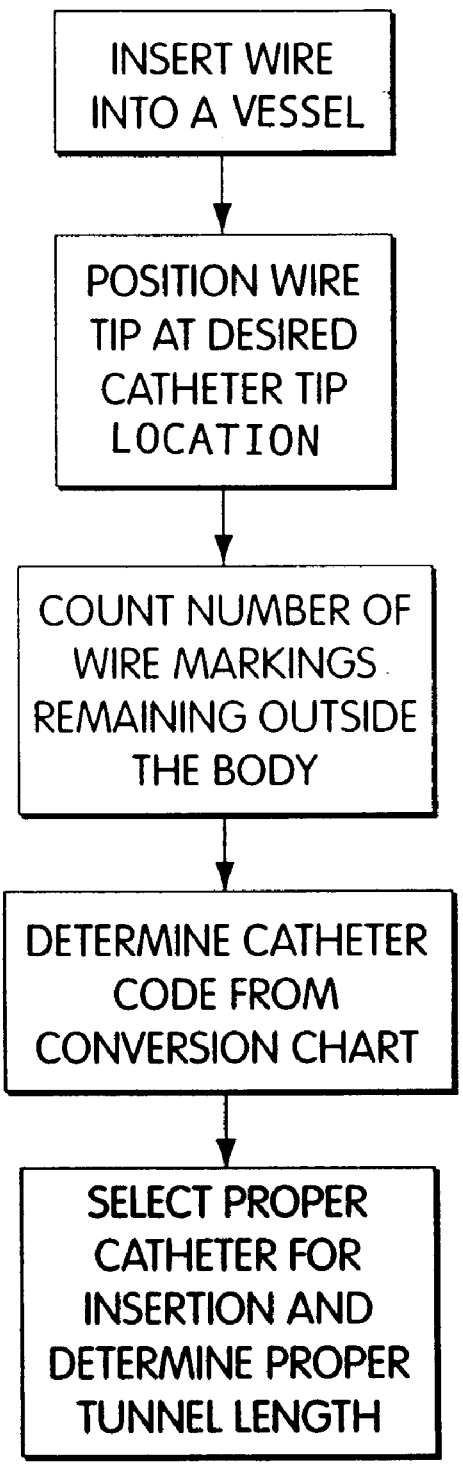
FIG. 5 is a flow chart illustrating a preinsertion measurement method for selecting a proper length catheter for insertion in a vessel of a body in accordance with the principles of the invention.

A method of the invention is illustrated in FIG. 5. Methods of the invention include inserting a wire, as described above, into a vessel of a body, positioning the tip of the wire at a desired catheter tip location, counting the number of markings on the portion of the wire remaining outside the body, and determining proper catheter and tunnel lengths based on this number of markings. As shown in FIG. 5, the determination of proper catheter and tunnel lengths from the number of markings on the portion of the wire remaining outside the body may be accomplished by referring to a conversion chart containing codes for catheters having particular lengths, as described above.

In one embodiment, the tip of the wire is radio-opaque. The wire may therefore be positioned using imaging techniques, such as fluoroscopy. In other embodiments, other imaging techniques, such as ultrasound, may also be used to position the tip of the wire.

In one embodiment, the proper catheter length is determined by using the number of markings on the portion of the wire remaining outside the body to calculate the length of wire outside the body, as described above. This length of wire is then located on a conversion chart, as described above, and the length of wire is then matched to proper catheter and tunnel lengths based on the chart. In an alternative embodiment, the length of wire remaining outside the body may be used to calculate the length of wire inside the body by subtracting the length remaining outside the body from the overall predetermined length of the wire. The length of wire in the body is then located in a conversion chart that converts lengths of wire inside the body to proper catheter and tunnel lengths. In another embodiment, the length of wire remaining outside the body (or, alternatively, the length of wire inside the body) is located in the conversion chart and matched with a code, which corresponds to a catheter having the proper catheter length.

The described kits and methods of the invention offer several advantages. First, kits and methods of the invention allow for determination of a proper catheter length before a sterile catheter kit is opened. This eliminates, or at least reduces, human error associated with selecting a catheter of incorrect length, and it avoids the wasted cost associated with opening a sterile catheter kit that includes a catheter of incorrect length. Second, when inserting a dialysis catheter, the physician can use the sterile ruler in the kit to determine the exact spot on the chest wall to create the tunnel. When a physician creates a tunnel that is not the correct length, the cost of the procedure increases due to the need to create a new tunnel, the increased chance of infection and hematoma, the increased procedure time, and the need to open a new sterile catheter kit. Third, the kits and methods of the invention provide "ease-of-insertion," which is an important consideration for interventional radiologists. Kits and methods of the invention simply make it easier for radiologists to place catheters, particularly dialysis catheters or other catheters that cannot be trimmed to a desired length.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A kit for use in performing preinsertion measurements to determine proper catheter and tunnel lengths for insertion of a catheter into a lumen of a body, comprising:
   (a) a wire of predetermined length, said wire having a tip, a proximal end, and a plurality of markings, each of said markings being at a predefined interval along said wire; and
   (b) a conversion chart for determining said proper catheter and tunnel lengths based on a length of said wire, said wire being insertable into said lumen so that said tip of said wire is positioned at a desired catheter tip location and said length of said wire being determined based on a number of said markings on a portion of said wire remaining outside said body after insertion of said wire into said lumen.

2. The kit of claim 1, wherein said tip is radio-opaque.

3. The kit of claim 1, further comprising an entry needle.

4. The kit of claim 1, further comprising a coaxial dilator assembly.

5. The kit of claim 1, further comprising a peelable sheath/dilator assembly.

6. The kit of claim 1, further comprising a sterile ruler.

7. The kit of claim 1, wherein said catheter is selected from the group consisting of a chronic dialysis catheter, a central port, and a tunneled central catheter.

8. The kit of claim 1, wherein said catheter is preattached to a subcutaneously implanted port.

9. The kit of claim 1, wherein said conversion chart contains a plurality of code numbers, each of which corresponds to a catheter of a particular length.

10. The kit of claim 9, wherein a code corresponding to a catheter having said proper catheter length is determined based on said length of said wire.

11. The kit of claim 1, wherein said length of said wire is a length of wire outside said body.

12. The kit of claim 1, wherein said length of said wire is a length of wire inside said body.

13. A method of determining a proper catheter length prior to insertion of said catheter into a lumen of a body, comprising the steps of:
 (a) inserting a wire of predetermined length into said lumen, said wire having a tip, a proximal end, and a plurality of markings, each of said markings being at a predefined interval along said wire;
 (b) positioning said tip of said wire at a desired catheter tip location;
 (c) counting a number of said markings on a portion of said wire remaining outside of said body; and
 (d) determining a proper catheter length based on said number of markings.

14. The method of claim 13, wherein said tip is radio-opaque.

15. The method of claim 14, wherein said positioning step is accomplished using fluoroscopy.

16. The method of claim 13, wherein said positioning step is accomplished using ultrasound.

17. The method of claim 13, wherein said determining step comprises the steps of:
 (a) determining a length of said wire outside said body based on said number of markings;
 (b) locating on a conversion chart said length of said wire outside said body; and
 (c) matching said length of said wire outside said body to said proper catheter length based on said chart.

18. The method of claim 13, wherein said determining step comprises the steps of:
 (a) determining a length of said wire inside said body based on said number of markings;
 (b) locating on a conversion chart said length of said wire inside said body; and
 (c) matching said length of said wire inside said body to said proper catheter length based on said chart.

19. The method of claim 17 or 18, wherein said matching step comprises the step of matching said length of said wire to a code number contained on said chart, wherein said code number corresponds to a catheter having said proper catheter length.

20. The method of claim 19, further comprising the step of determining a proper tunnel length based on said code.

21. The method of claim 13, wherein said catheter is selected from the group consisting of a chronic dialysis catheter, a central port, and a tunneled central catheter.

22. The method of claim 13, wherein said catheter is preattached to a subcutaneously implanted port.

* * * * *